(12) United States Patent
Noguchi

(10) Patent No.: US 9,888,907 B2
(45) Date of Patent: *Feb. 13, 2018

(54) ULTRASOUND DIAGNOSTIC APPARATUS AND ULTRASOUND IMAGE PRODUCING METHOD

(71) Applicant: FUJIFILM Corporation, Tokyo (JP)

(72) Inventor: Masafumi Noguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/412,549

(22) Filed: Jan. 23, 2017

(65) Prior Publication Data

US 2017/0128048 A1    May 11, 2017

Related U.S. Application Data

(63) Continuation of application No. 14/520,471, filed on Oct. 22, 2014, now Pat. No. 9,585,637.

(30) Foreign Application Priority Data

Jan. 16, 2014  (JP) ................................ 2014-006088

(51) Int. Cl.
    *A61B 8/08*    (2006.01)
    *A61B 8/00*    (2006.01)
    *A61B 8/14*    (2006.01)

(52) U.S. Cl.
    CPC ............ *A61B 8/5207* (2013.01); *A61B 8/145* (2013.01); *A61B 8/4494* (2013.01); *A61B 8/5253* (2013.01)

(58) Field of Classification Search
    CPC ..... A61B 8/145; A61B 8/4494; A61B 8/5207; A61B 8/5253
    See application file for complete search history.

(56) References Cited

U.S. PATENT DOCUMENTS

| 9,585,637 B2 * | 3/2017 | Noguchi ............ A61B 8/5207 |
| 2017/0128049 A1 * | 5/2017 | Noguchi ............ A61B 8/5207 |

FOREIGN PATENT DOCUMENTS

| JP | 2012-200514 A | 10/2012 |
| JP | 2013-141519 A | 7/2013 |

OTHER PUBLICATIONS

Japanese Office Action, dated Dec. 8, 2015, for Japanese Application No. 2014-006088, including English translation.

(Continued)

*Primary Examiner* — Michael Rozanski
(74) *Attorney, Agent, or Firm* — Birch, Stewart, Kolasch & Birch, LLP

(57) ABSTRACT

Disclosed are an ultrasound diagnostic apparatus and an ultrasound image producing method capable of producing a spatial compound image with reduced artifacts. Reception data of frame images is repeatedly acquired in a data acquisition cycle of four frames such that, of three frame images for use in producing a spatial compound image, the angle difference in steering angle between two frames for which the acquisition of reception data is most temporally separated is smaller than a maximum value among the angle differences in steering angle between two frame images among three frame images having different steering angles, and each time reception data of two frame images or reception data of another two frame images is acquired, three frame images sequentially produced based on reception data for three frames sequentially acquired hitherto are synthesized to produce a spatial compound image.

17 Claims, 8 Drawing Sheets

(56) References Cited

OTHER PUBLICATIONS

U.S. Non-Final Office Action, dated Aug. 1, 2016, for U.S. Appl. No. 14/520,471.
U.S. Notice of Allowance, dated Nov. 18, 2016, for U.S. Appl. No. 14/520,471.

* cited by examiner

ULTRASOUND DIAGNOSTIC APPARATUS AND ULTRASOUND IMAGE PRODUCING METHOD

CROSS-REFERENCE TO RELATED APPLICATIONS

This application is a Continuation of U.S. patent application Ser. No. 14/520,471 filed on Oct. 22, 2014, (now U.S. Pat. No. 9,585,637 issued Mar. 7, 2017), which claims priority under 35 U.S.C. § 119 to Japanese Patent Application No. 2014-006088, filed on Jan. 16, 2014. Each of the above application(s) is hereby expressly incorporated by reference, in its entirety, into the present application.

BACKGROUND OF THE INVENTION

1. Field of the Invention

The present invention relates to an ultrasound diagnostic apparatus and an ultrasound image producing method, and in particular, to an ultrasound diagnostic apparatus and an ultrasound image producing method which synthesize a plurality of frame images having different steering angles of an ultrasonic beam to produce an update image (spatial compound image).

2. Description of the Related Art

An ultrasound diagnostic apparatus using an ultrasound image has hitherto been put into practical use in the field of medicine. In general, in this type of ultrasound diagnostic apparatus, an ultrasound image is produced by transmitting an ultrasonic beam from a transducer array having a plurality of transducers arranged therein toward a subject, receiving an ultrasonic echo from the subject by the transducer array, and electrically processing the reception signal.

In the ultrasound diagnostic apparatus, while a two-dimensional tomographic image in the subject can be acquired in real time by scanning the ultrasonic beam, a plurality of reflected waves from a fine structure in the subject interfere with one another to cause speckle noise, and speckle noise is one of the factors for causing deterioration in image quality of the ultrasound image.

As a method of reducing speckle noise, for example, a spatial compounding method disclosed in JP 2013-141519 A is known. In the spatial compounding method, a plurality of frame images are produced by transmitting an ultrasonic beam from different directions toward the same region in the subject, and a plurality of frame images are synthesized to produce one spatial compound image. Since the pattern of speckle noise fluctuates according to the transmission direction of the ultrasonic beam, a plurality of frame images produced by transmitting the ultrasonic beam from different directions are synthesized, whereby it is possible to reduce speckle noise.

For example, as shown in FIG. 12, a frame image A based on reception data acquired by transmitting and receiving an ultrasonic beam in a direction perpendicular to a transducer array, that is, in a direction of a steering angle of 0 degrees, a frame image B based on reception data acquired by transmitting and receiving an ultrasonic beam in a direction of a steering angle −a, and a frame image C based on reception data acquired by transmitting and receiving an ultrasonic beam in a direction of a steering angle +a are repeatedly produced in a three-frame cycle in the same order, and each time reception data of one frame is acquired, the frame images for three frames including previous two frame images are synthesized to produce a spatial compound image. With this, the spatial compound image made from the frame images A, B, and C corresponding to the three kinds of steering angles is constantly updated.

However, in the ultrasound image, in addition to speckle noise, patterns, such as acoustic shadow, different from an actual structure are produced, and these patterns are generated to have different shapes at different angles according to the steering angle of the ultrasonic beam to be transmitted and received. For this reason, if the inside of the subject is about to be observed by the spatial compound image to be sequentially updated while moving the transducer array along the body surface of the subject, the pattern shapes and angles of speckle noise and acoustic shadow fluctuate for each frame, and as a result, there is a problem in that artifacts in which an image vibrates like a wave occur.

SUMMARY OF THE INVENTION

The invention has been accomplished in order to solve the problem in the related art, and an object of the invention is to provide an ultrasound diagnostic apparatus and an ultrasound image producing method capable of producing a spatial compound image with reduced artifacts. The inventors have carefully studied artifacts which occur when a synthesis condition of a plurality of frame images changes in various ways to produce many spatial compound images (motion image) and have found that the larger the moving distance of the transducer array among a plurality of frame images to be synthesized and the larger the angle difference in steering angle among a plurality of frame images to be synthesized, the more the artifacts are deteriorated.

In a synthesis method of the related art shown in FIG. 12, since the synthesis of the three frame images is performed each time reception data of one frame image is acquired, the order of the three frame images to be synthesized changes each time a spatial compound image is updated. For example, if it is assumed that, among the three frame images for use in producing one spatial compound image, reception data of the frame image A is acquired as a first frame F1, reception data of the frame image B is acquired as a second frame F2, and reception data of the frame image C is acquired as a third frame F3, in producing the next spatial compound image to be updated, reception data is acquired such that the frame image A is allocated as the first frame F1, the frame image B is allocated as the second frame F2, and the frame image C is allocated as the third frame F3.

For this reason, as shown in FIG. 13, a combination in which, among the three frame images to be synthesized, the frame image C of the steering angle +a is allocated as the first frame F1 for which reception data is acquired at the earliest time t1 and the frame image C of the steering angle −a is allocated as the third frame F3 for which reception data is acquired at the latest time t3 is generated cyclically, and at this time, the angle difference Δθ in steering angle between the frame F1 and the frame F3 becomes a maximum value 2·a. In this way, it is considered that, when synthesizing ultrasound images for three frames while moving the transducer array, in the first frame F1 and the third frame F3 for which the moving distance of the transducer array is largest, a state in which the angle difference in steering angle becomes a maximum angle difference among the angle differences in steering angle between two frame images among the three frame images A to C for use in producing a spatial compound image occurs, causing deterioration in artifacts.

Since the faster a frame rate, the shorter the moving distance of an ultrasound probe in a reception data acquisition period of one frame image, it is understood that artifacts are hardly visually recognized. However, in order to increase the frame rate, it is necessary to reduce the scan line density of the ultrasound image and the number of focal points. When a harmonic image of a pulse inversion method is used, a measure, such as stopping pulse inversion scanning and using an image by a fundamental harmonic, is required, causing degradation in image quality.

As shown in FIG. 14, while reception data of each frame image is repeatedly acquired in a three-frame cycle, each time reception data of three frame images is acquired, if the three frame images are synthesized to update a spatial compound image, since the order of the three frame images for use in producing the spatial compound image is fixed, it is observed that a time-series overlapping method of patterns, such as speckle noise and acoustic shadow, is stable, and artifacts hardly occur. However, since synthesis is performed each time reception data of the three frame images is acquired, the update rate of the spatial compound image becomes ⅓, and operationality as the ultrasound diagnostic apparatus is degraded.

Accordingly, in the invention, artifacts are reduced while suppressing degradation in image quality and degradation in operationality.

An ultrasound diagnostic apparatus according to an aspect of the invention includes a transducer array, a transmitter which supplies an actuation signal to the transducer array to transmit an ultrasonic beam from the transducer array toward a subject, a receiver which processes a reception signal output from the transducer array having received an ultrasonic echo by the subject to acquire reception data, a transmission and reception controller which controls the transmitter and the receiver such that reception data of n (where n is an integer equal to or greater than 3) frame images is sequentially repeatedly acquired in order to synthesize n frame images having different steering angles of the ultrasonic beam to produce an update image, and the angle difference in steering angle between two frame images, for which the acquisition of reception data is most temporally separated, among the n frame images for use in producing the update image is smaller than a maximum angle difference among the angle differences in steering angle between two frame images among the n frame images, and an update image producer which produces each update image based on reception data acquired by the receiver.

Here, the steering angle refers to an angle between the direction of the ultrasonic beam to be transmitted and received and a direction perpendicular to the arrangement direction of a plurality of ultrasound transducers constituting the transducer array. The frame images refer to individual ultrasound images when a plurality of ultrasound images having different steering angles of the ultrasonic beam are synthesized to produce one update image.

It is preferable that the transmission and reception controller controls the transmitter and the receiver such that the angle difference in steering angle between two frame images, for which the acquisition of reception data is most temporally separated, among the n frame images for use in producing each update image becomes a minimum angle difference among the angle differences in steering angle between two frame images among the n frame images.

Each time reception data of m (where m is an integer which satisfies 1≤m<n) frame images is acquired by the receiver, the update image producer may synthesize the previous n frame images, for which reception data is sequentially acquired hitherto, to produce the update image.

The transmission and reception controller may control the transmitter and the receiver such that, when n is an odd number, reception data of n+1 frame images obtained by adding a new frame image having the same steering angle of the ultrasonic beam as a k-th (k=(n+1)/2) specific frame image among the n frame images to the n frame images as an (n+1)th frame image is sequentially repeatedly acquired, and each time reception data of k frame images is acquired by the receiver, the update image producer may synthesize the previous n frame images, for which reception data is sequentially acquired hitherto, to produce the update image.

In this case, it is preferable that the specific frame image is a frame image having a maximum steering angle among the n frame images for use in producing each update image.

An ultrasound image producing method according to another aspect of the invention includes performing transmission and reception of an ultrasonic beam by a transducer array such that reception data of n (where n is an integer equal to or greater than 3) frame images is sequentially repeatedly acquired in order to synthesize n frame images having different steering angles of the ultrasonic beam to produce an update image, and the angle difference in steering angle between two frame images, for which the acquisition of reception data is most temporally separated, among the n frame images for use in producing the update image is smaller than a maximum angle difference among the angle differences in steering angle between two frame images among the n frame images, and producing each update image based on the acquired reception data.

According to the aspects of the invention, the transmission and reception of the ultrasonic beam by the transducer array are performed such that reception data of n (where n is an integer equal to or greater than 3) frame images is sequentially repeatedly acquired in order to synthesize the n frame images having different steering angles of the ultrasonic beam to produce an update image, and the angle difference in steering angle between two frame images, for which the acquisition of reception data is most temporally separated, among the n frame images for use in producing each update image is smaller than a maximum angle difference among the angle differences in steering angle between two frame images among the n frame images. For this reason, it is possible to produce an update image (spatial compound image) with reduced artifacts.

DESCRIPTION OF THE PREFERRED EMBODIMENTS

Hereinafter, embodiments of the invention will be described referring to the accompanying drawings.

Embodiment 1

Figure 1:
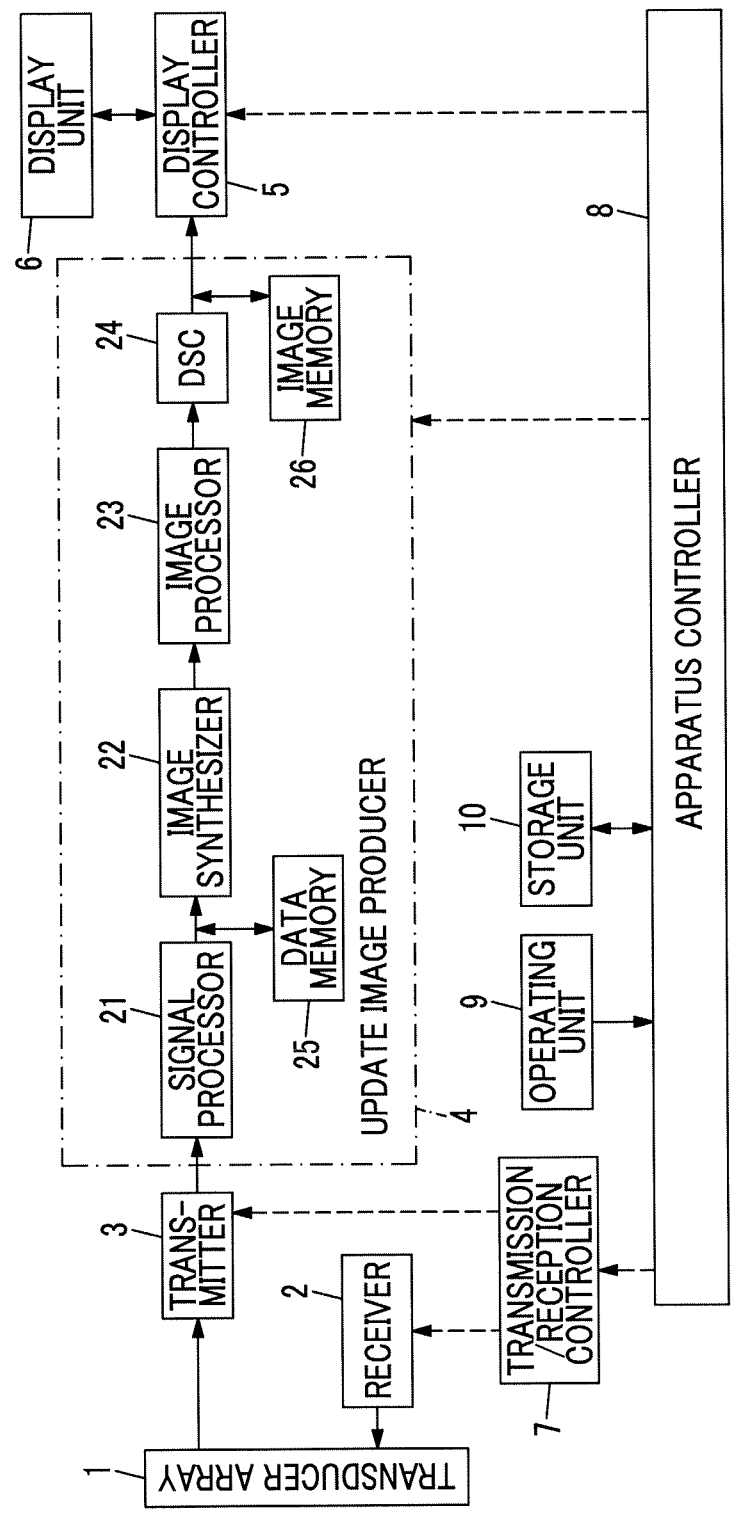
FIG. 1 is a block diagram showing the configuration of an ultrasound diagnostic apparatus according to Embodiment 1 of the invention.

FIG. 1 shows the configuration of an ultrasound diagnostic apparatus according to Embodiment 1 of the invention. The ultrasound diagnostic apparatus has a transducer array 1, a transmitter 2 and a receiver 3 are connected to the transducer array 1, and an update image producer 4 is connected to the receiver 3. A display controller 5 is connected to the update image producer 4, and a display unit 6 is connected to the display controller 5. A transmission and reception controller 7 is connected to the transmitter 2 and the receiver 3, and an apparatus controller 8 is connected to the update image producer 4, the display controller 5, and the transmission and reception controller 7. An operating unit 9 and a storage unit 10 are connected to the apparatus controller 8.

The update image producer 4 produces an update image (a spatial compound image to be sequentially updated), and has a signal processor 21 connected to the receiver 3. An image synthesizer 22, an image processor 23, and a digital scan converter (DSC) 24 are sequentially connected to the signal processor 21, a data memory 25 is connected to the signal processor 21, and an image memory 26 is connected to the DSC 24.

The transducer array 1 has a plurality of ultrasound transducers arranged in a one-dimensional or two-dimensional manner. Each ultrasound transducer transmits an ultrasonic wave according to an actuation signal supplied from the transmitter 2 and receives an ultrasonic echo from a subject to output a reception signal. Each ultrasound transducer is constituted by a vibrator in which electrodes are formed at both ends of a piezoelectric substance made of piezoelectric ceramic represented by PZT (lead zirconate titanate), a polymer piezoelectric element represented by PVDF (polyvinylidene difluoride), piezoelectric single crystal represented by PMN-PT (lead magnesium niobate-lead titanate solid solution), or the like.

If a pulsed or continuous-wave voltage is applied to the electrodes of the vibrator, the piezoelectric substance expands and contracts, whereby pulsed or continuous-wave ultrasonic waves are generated from the vibrators, and an ultrasonic beam is formed by synthesizing the ultrasonic waves. When receiving the propagating ultrasonic waves, the respective vibrators expand and contract to generate electrical signals, and the electrical signals are output as the reception signals of the ultrasonic waves.

The transmitter 2 includes, for example, a plurality of pulse generators, adjusts the delay amount of each of actuation signals based on a transmission delay pattern selected according to a control signal supplied from the transmission and reception controller 7 such that the ultrasonic waves transmitted from the plurality of ultrasound transducers of the transducer array 1 forming a transmission opening form an ultrasonic beam, and supplies the adjusted actuation signals to the plurality of ultrasound transducers.

The receiver 3 amplifies the reception signal output from each ultrasound transducer of the transducer array 1 and performs A/D conversion to produce digitized reception data.

The update image producer 4 updates a spatial compound image made from a plurality of frame images based on reception data acquired by the receiver 3 at a predetermined update rate to produce the spatial compound image as a motion image.

The signal processor 21 executes reception focus processing and detection processing on reception data produced by the receiver 3 corresponding to the plurality of ultrasound transducers of the transducer array 1 based on a command signal from the apparatus controller 8 to produce B-mode image signals. That is, reception data generated by the receiver 3 is subjected to the corresponding delay correction to produce delay-corrected data, and delay-corrected data is added, whereby the focus of the ultrasonic echo is narrowed to produce a sound ray signal. Furthermore, attenuation according to the depth of the reflection point of the ultrasonic wave is corrected for the produced sound ray signal, envelope detection processing is performed, log compression is performed to produce B-mode image signals, and the B-mode image signals are output to the data memory 25.

The image synthesizer 22 synthesizes B-mode image signals for a plurality of frames stored in the data memory 25 under the control of the apparatus controller 8 to produce a spatial compound image signal and outputs the spatial compound image signal to the image processor 23. Here, the term "synthesis" refers to the calculation of the mean value of the B-mode image signals for a plurality of frames for each pixel. Various kinds of mean calculation, such as arithmetic mean and geometric mean, can be used.

The image processor 23 performs various kinds of necessary image processing, such as gradation processing, on the spatial compound image signal produced by the image synthesizer 22, and outputs the spatial compound image signal to the DSC 24.

The DSC 24 converts (raster-converts) the spatial compound image signal subjected to image processing by the image processor 23 to an image signal according to a television signal scan system, stores the image signal in the image memory 26, and outputs the image signal to the display controller 5.

The display controller 5 causes the display unit 6 to display a spatial compound image as an update image based on the image signal converted by the DSC 24 or the image signal stored in the image memory 26.

The display unit 6 includes, for example, a display device, such as an LCD, and displays the spatial compound image under the control of the display controller 5.

The transmission and reception controller 7 controls the operations of the transmitter 2 and the receiver 3 based on a command signal from the apparatus controller 8.

The apparatus controller 8 controls the respective units of the ultrasound diagnostic apparatus based on a command input from the operating unit 9 by an operator.

The operating unit 9 is used when the operator performs an input operation, and can be formed of a keyboard, a mouse, a trackball, a touch panel, or the like.

The storage unit 10 stores an operating program or the like, and a recording medium, such as a hard disk, a flexible disk, a magnetic optical disk (MO disk), a masking tape (MT), a random access memory (RAM), a compact disk-read only memory (CD-ROM), a digital versatile disc-read only memory (DVD-ROM), a secure digital card (SD card), a compact flash card (CF card), a universal serial bus memory (USB memory), or a server may be used.

Although the signal processor 21, the image synthesizer 22, the image processor 23, and the DSC 24 of the update image producer 4, the display controller 5, and the transmission and reception controller 7 are constituted by a CPU and an operating program for causing the CPU to perform various kinds of processing, these units may be constituted by digital circuits.

Here, a transmission and reception method of an ultrasonic wave and a synthesis method of reception data in Embodiment 1 will be described.

Figure 2:
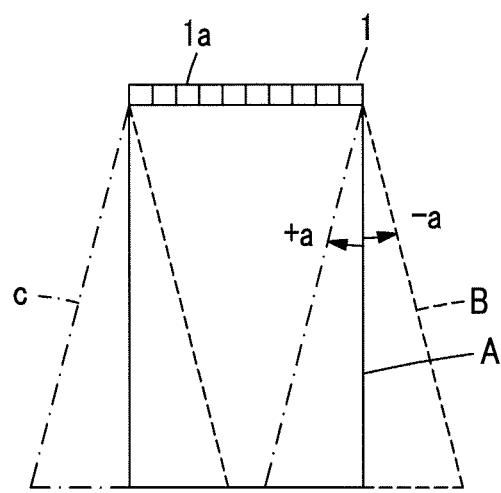
FIG. 2 is a diagram showing steering angles of three kinds of frame images in Embodiment 1.

In Embodiment 1, as shown in FIG. 2, frame images corresponding three kinds of steering angles including a frame image A based on reception data acquired by transmitting and receiving an ultrasonic beam in a direction perpendicular to the arrangement direction of the plurality of ultrasound transducers 1*a* constituting the transducer array 1, that is, in a direction of a steering angle of 0 degrees, a frame image B based on reception data acquired by the transmitting and receiving an ultrasonic beam in a direction of a steering angle −a, and a frame image C based on reception data acquired by transmitting and receiving an ultrasonic beam in a direction of a steering angle +a are produced.

That is, while the angle differences in steering angle between the frame image A and the frame image B and between the frame image A and the frame image C are respectively "0", a maximum angle difference 2·a among the angle differences in steering angle between two frame images among the three kinds of frame images A to C is formed between the frame image B and the frame image C.

Figure 12:
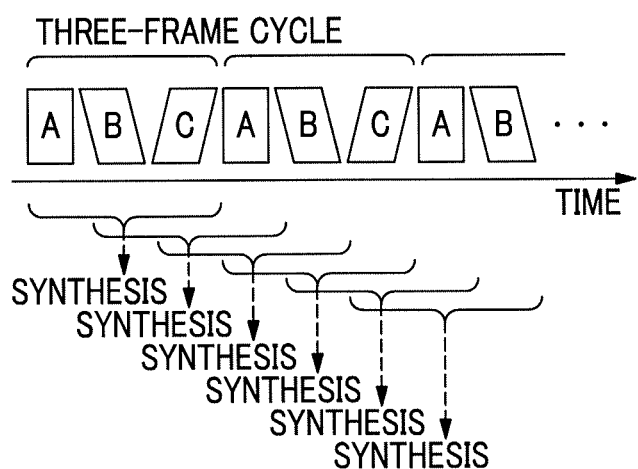
FIG. 12 is a diagram showing the relationship between a data acquisition cycle and frame image synthesis in a related art example.
Figure 13:
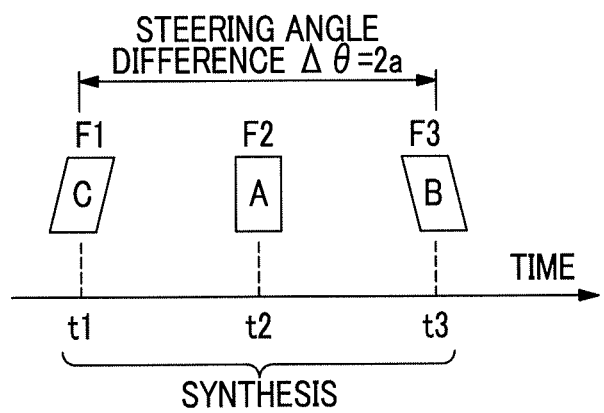
FIG. 13 is a diagram showing the angle difference in steering angle between a first frame and a third frame among three frame images for use in producing a spatial compound image in the related art example.

For this reason, as in the related art example shown in FIG. 12, if reception data corresponding to the frame images A to C is repeatedly acquired in a three-frame cycle in the same order, and each time reception data of one frame is acquired, ultrasound images for three frames including images of previous two frames are synthesized to produce a spatial compound image, among the three frame images for use in producing the spatial compound image, the frame image C of the steering angle +a and the frame image B of the steering angle −a are respectively allocated as the first frame F1 and the third frame F3 for which the acquisition time of reception data is most separated, and a combination in which the maximum angle difference 2·a in steering angle is formed between these frames F1 and F3 is generated cyclically, causing deterioration in artifacts.

Figure 3:
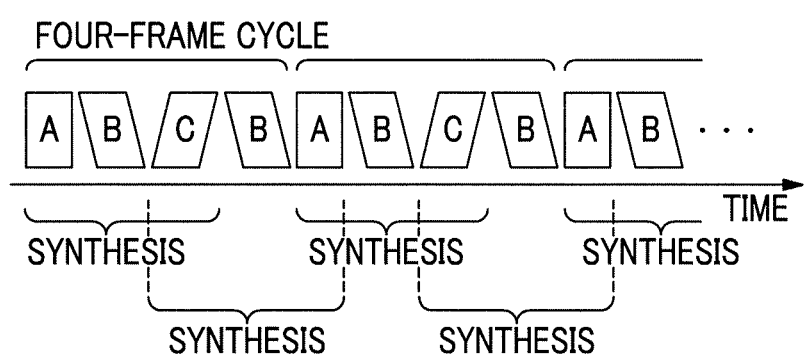
FIG. 3 is a diagram showing the relationship between a data acquisition cycle and frame image synthesis in Embodiment 1.

Accordingly, in Embodiment 1, as shown in FIG. 3, the transmission and reception controller 7 controls the operations of the transmitter 2 and the receiver 3 such that reception data corresponding to the first frame image A of the steering angle of 0 degrees, reception data corresponding to the second frame image B of the steering angle −a, and reception data corresponding to the third frame image C of the steering angle +a are acquired, then, reception data is acquired at the same steering angle −a as the second frame image B ordered at the center of the first to third frame images A to C to form a new fourth frame image B, and reception data of these four frame images is sequentially repeatedly acquired. That is, reception data corresponding to the frame images A, B, C, and B is repeatedly acquired in the data acquisition cycle of four frames.

The apparatus controller 8 controls the operation of the image synthesizer 22 such that, each time reception data of the two frame images B and C or reception data of the two frame images B and A is acquired, three frame images sequentially produced by the update image producer 4 based on reception data for previous three frames sequentially acquired hitherto are synthesized to produce a spatial compound image. For example, if reception data of the third frame image C is acquired in one data acquisition cycle in which reception data of four frames is sequentially acquired, three frame images including the frame image C produced based on reception data and the previous two frame images A and B are synthesized to produce a spatial compound image, thereafter, image synthesis is not performed when reception data of the fourth frame image B is acquired, and when reception data of the first frame image A is acquired in the next data acquisition cycle, three frame images including the frame image A produced based on reception data and the previous two frame images, that is, the third frame image C and the fourth frame image B in the previous data acquisition cycle to produce a spatial compound image.

In this way, each time reception data of two frame images is acquired, three frame images based on reception data for three frames sequentially acquired hitherto are synthesized to produce a spatial compound image, whereby, among the three frame images for use in producing the spatial compound image, the frame image B is constantly allocated as the second frame F2 located at the center in a time-series manner, the frame image A is allocated in one of the first frame F1 and the third frame F3, and the frame image C is allocated in the other frame.

Figure 4:
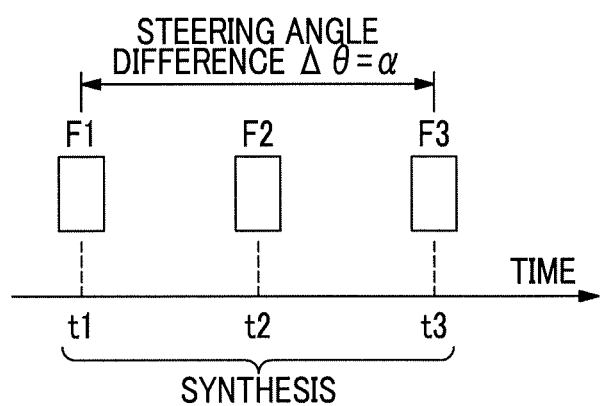
FIG. 4 is a diagram showing the angle difference in steering angle between a first frame and a third frame among three frame images for use in producing a spatial compound image in Embodiment 1.

That is, as shown in FIG. 4, among three frame images to be synthesized, a combination of the first frame F1 for which reception data is acquired at the earliest time t1 and the third frame F3 for which reception data is acquired at the latest time t3 constantly become the frame image A of the steering angle of 0 degrees and the frame image C of the steering angle +a, and the angle difference Δθ in steering angle between the frame F1 and the frame F3 becomes "a".

For this reason, even if frame images are synthesized three by three to perform spatial compounding while moving the transducer array 1 along the body surface of the subject, a state in which, among the three frame images for use in producing the spatial compound image, the angle difference Δθ in steering angle between the first frame F1 and the third frame F3, for which the moving distance of the transducer array 1 is largest, becomes the maximum value 2·a is not generated, and it is possible to reduce artifacts compared to the related art example shown in FIG. 12.

Figure 14:
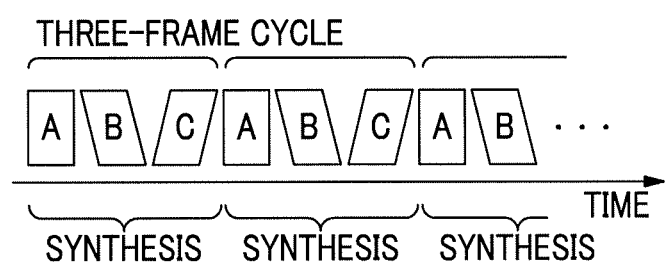
FIG. 14 is a diagram showing the relationship between a data acquisition cycle and frame image synthesis in another related art example.

Each time reception data of two frames is acquired, since synthesis of ultrasound images is performed, the update rate of the compound image becomes ½ compared to the related art example shown in FIG. 12 where frame images are synthesized each time reception data of one frame is acquired. Meanwhile, there is no case where the image update rate is lowered to ⅓ as in the related art example shown in FIG. 14 where ultrasound images are synthesized each time reception data of three frames to be synthesized is acquired, and it is possible to reduce artifacts while suppressing degradation in operationality.

Next, the operation of Embodiment 1 will be described.

First, if a command to execute spatial compounding is input from the operating unit 9 by the operator, as shown in FIG. 3, a command signal is output from the apparatus controller 8 to the transmission and reception controller 7 such that reception data corresponding to the first frame image A, reception data corresponding to the second frame image B, and reception data corresponding to the third frame image C are sequentially acquired, then, reception data corresponding to the fourth frame image B at the same steering angle as the second frame image B is acquired, and reception data of these four frame images is sequentially repeatedly acquired in this order.

With this, first, the ultrasonic beam is transmitted from the transducer array 1 in the direction of the steering angle of 0 degrees by the transmitter 2, and the reception signal output from the transducer array 1 having received the ultrasonic echo by the subject is processed by the receiver 3 to acquire reception data of the first frame image. Reception data is transmitted to the signal processor 21 of the update image producer 4, delay-corrected data is produced by subjecting delay correction to reception data such that reception focus is performed in the direction of the steering angle of 0 degrees, and the sound ray signal is produced by adding delay-corrected data. Furthermore, attenuation according to the depth of the reflection position of the ultrasonic wave is corrected for the sound ray signal, then, envelope detection processing and log compression are performed to produce the B-mode image signal of the frame image A, and the B-mode image signal is stored in the data memory 25.

Subsequent to the acquisition of reception data of the first frame image, the ultrasonic beam is transmitted from the transducer array 1 in the direction of the steering angle −a by the transmitter 2, reception data of the second frame image is acquired by the receiver 3, and similarly, the B-mode image signal of the frame image B is produced by the signal processor 21 of the update image producer 4 and stored in the data memory 25.

Subsequent to the acquisition of reception data of the second frame image, the ultrasonic beam is transmitted from the transducer array 1 in the direction of the steering angle +a by the transmitter 2, reception data of the third frame image is acquired by the receiver 3, and similarly, the B-mode image signal of the frame image C is produced by the signal processor 21 of the update image producer 4 and stored in the data memory 25.

In this way, if reception data of the first to third frame images are sequentially acquired, and the three B-mode image signal of the frame images A to C are produced by the signal processor 21 of the update image producer 4 and stored in the data memory 25, the image synthesizer 22 synthesizes the frame images A to C for three frames stored in the data memory 25 to produce a spatial compound image signal based on a command signal from the apparatus controller 8. The spatial compound image signal is subjected to image processing, such as gradation processing, by the image processor 23, is raster-converted by the DSC 24, is then output to the display controller 5, and is displayed on the display unit 6 by the display controller 5.

Subsequent to the acquisition of reception data of the third frame image, similarly to the second frame image, the ultrasonic beam is transmitted from the transducer array 1 in the direction of the steering angle −a by the transmitter 2, reception data of the fourth frame image is acquired by the receiver 3, and the B-mode image signal of the frame image B is produced by the signal processor 21 of the update image producer 4 and stored in the data memory 25.

With this, one data acquisition cycle in which reception data of the first to fourth frame images is acquired ends, subsequently, the ultrasonic beam is transmitted from the transducer array 1 in the direction of the steering angle of 0 degrees by the transmitter 2, reception data of the first frame image is acquired by the receiver 3 in the next data acquisition cycle, and the B-mode image signal of the frame image A is produced by the signal processor 21 of the update image producer 4 and stored in the data memory 25.

In this way, if reception data of two frame images including the fourth frame image in the previous data acquisition cycle and the first frame image in the next data acquisition cycle is acquired, the image synthesizer 22 synthesizes three frame images based on reception data for three frames sequentially acquired hitherto, that is, the third frame image C and the fourth frame image B in the previous data acquisition cycle and the first frame image A in the next data acquisition cycle to produce a spatial compound image signal. The spatial compound image signal passes through the image synthesizer 22, the image processor 23, and the DSC 24, and is then displayed on the display unit 6 by the display controller 5, and the spatial compound image is updated.

Similarly, each time reception data of two frame images is acquired, three frame images based on reception data for three frames sequentially acquired hitherto are produced by the signal processor 21 of the update image producer 4, and the spatial compound image sequentially updated is produced by the image synthesizer 22. At this time, among the three frame images for use in producing the spatial compound image, the frame image A is allocated in one of the first frame F1 and the third frame F3, and the frame image C is allocated in the other frame. For this reason, the angle difference in steering angle between the two frames F1 and F3, for which the acquisition of reception data is most temporally separated, constantly becomes "a" and is smaller than the maximum angle difference 2·a among the angle differences in steering angle between two frame images among the three kinds of frame images A to C. For this reason, even if the frame rate is not increased, it is possible to produce a spatial compound image with reduced artifacts.

In Embodiment 1, although reception data corresponding to the frame images A, B, C, and B are repeatedly acquired in the data acquisition cycle of four frames, and each time reception data of the two frame images B and C or reception data of the two frame images B and A is acquired, three frame images sequentially produced based on reception data for previous three frames sequentially acquired hitherto are synthesized to produce a spatial compound image, the invention is not limited thereto.

A combination in which, among the three frame images for use in producing the spatial compound image, the frame images B and C are respectively allocated in the first frame F1 and the third frame F3, for which the acquisition of reception data is most temporally separated, to form the maximum angle difference 2·a in steering angle should not be used.

For example, reception data of the frame images A, C, B, and C may be repeatedly acquired in the data acquisition cycle of four frames, and each time reception data of the two frame images C and B or reception data of the two frame images C and A is acquired, three frame images sequentially produced based on reception data for three frames sequentially acquired hitherto may be synthesized to produce a spatial compound image. In this case, among the three frame images for use in producing the spatial compound image, the angle difference in steering angle between the first frame F1 and the third frame F3, for which the acquisition of reception data is most temporally separated, constantly becomes "a" and is smaller than the maximum angle difference 2·a among the angle differences in steering angle between two frame images among the three kinds of frame images A to C. For this reason, it is possible to reduce artifacts.

In Embodiment 1 described above, although the frame images corresponding to the three kinds of steering angles including the frame image A of the steering angle of 0 degrees, the frame image B of the steering angle −a, the frame image C of the steering angle +a are produced, the invention is not limited thereto, and three kinds of frame images having different arbitrary steering angles may be produced to produce a spatial compound image.

At this time, a frame image having a maximum steering angle among the three kinds of frame images is allocated as a frame image for which reception data is acquired second in the data acquisition cycle of four frames and a frame image for which reception data is acquired fourth, whereby, among the three frame images for use in producing the spatial compound image, the angle difference in steering angle between the first frame F1 and the third frame F3, for which the acquisition of reception data is most temporally separated, can be made smaller than the maximum angle difference among the angle differences in steering angle between two frame images among the three kinds of frame images.

Embodiment 2

In Embodiment 1 described above, although three frame images are synthesized to produce a spatial compound image, an ultrasound diagnostic apparatus according to Embodiment 2 synthesizes five frame images to produce a high-quality spatial compound image with an improved speckle noise reduction effect. The configuration of the ultrasound diagnostic apparatus according to Embodiment 2 is the same as the ultrasound diagnostic apparatus of Embodiment 1 shown in FIG. 1.

Figure 5:
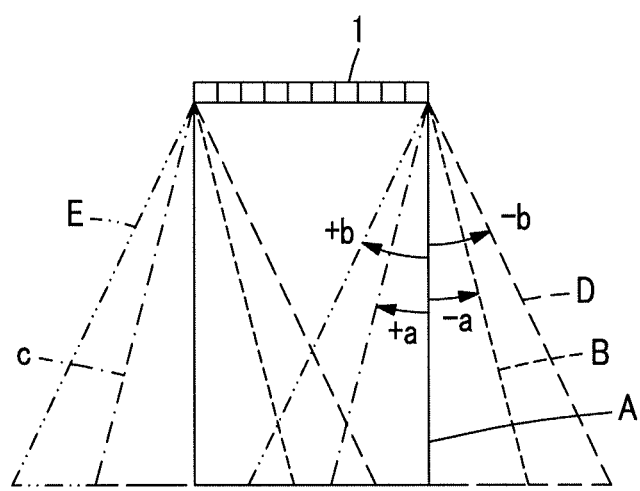
FIG. 5 is a diagram showing steering angles of five kinds of frame images in Embodiment 2.

In Embodiment 2, as shown in FIG. 5, frame images corresponding to five kinds of steering angles including a frame image A based on reception data acquired by transmitting and receiving an ultrasonic beam in a direction perpendicular to the arrangement direction of a plurality of ultrasound transducers 1a constituting the transducer array 1, that is, in a direction of a steering angle of 0 degrees, a frame image B based on reception data acquired by transmitting and receiving an ultrasonic beam in a direction of a steering angle −a, a frame image C based on reception data acquired by transmitting and receiving an ultrasonic beam in a direction of a steering angle +a, a frame image D based on reception data acquired by transmitting and receiving an ultrasonic beam in a direction of a steering angle −b, and a frame image E based on reception data acquired by transmitting and receiving an ultrasonic beam in a direction of a steering angle +b are produced. Here, it is assumed that the absolute value b of the steering angle of each of the frame images D and E is greater than the absolute value a of the steering angle of each of the frame images B and C, and an angle "b−a" is smaller than the angle a.

As will be understood from FIG. 5, a maximum angle difference 2·b among the angle differences in steering angle between two frame images among the five kinds of frame images A to E is formed between the frame image D and the frame image E, and a minimum angle difference "b−a" in steering angle is formed between the frame image B and the frame image D and between the frame image C and the frame image E.

Figure 6:
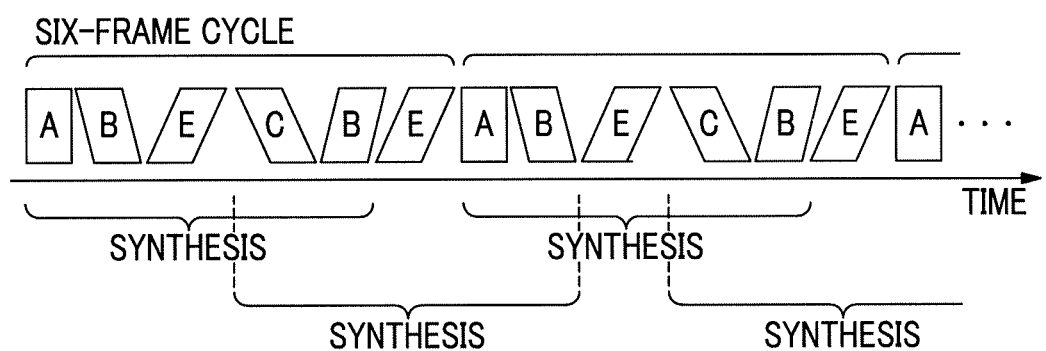
FIG. 6 is a diagram showing the relationship between a data acquisition cycle and frame image synthesis in Embodiment 2.

Then, as shown in FIG. 6, the transmission and reception controller 7 controls the operations of the transmitter 2 and the receiver 3 such that reception data corresponding to the first frame image A of the steering angle of 0 degrees, reception data corresponding to the second frame image B of the steering angle −a, reception data corresponding to the third frame image E of the steering angle +b, reception data corresponding to the fourth frame image D of the steering angle −b, and reception data corresponding to the fifth frame image C of the steering angle +a are sequentially acquired, then, reception data corresponding to the frame image E of the same steering angle +b as the third frame image ordered at the center of the first to fifth frame images is acquired to form a new sixth frame image, and reception data of these six frame images are sequentially repeatedly acquired. That is, reception data corresponding to the frame images A, B, E, D, C, and E are repeatedly acquired in a data acquisition cycle of six frames.

The apparatus controller 8 controls the operation of the image synthesizer 22 such that, each time reception data of the three frame images E, D, and C or reception data of the three frame images E, A, and B is acquired, five frame images sequentially produced by the signal processor 21 of the update image producer 4 based on reception data for five frames sequentially acquired hitherto are synthesized to produce a spatial compound image.

For example, if reception data of the fifth frame image is acquired in one data acquisition cycle in which reception data of six frame images are sequentially acquired, five frame images including the frame image C produced based on reception data and the previous four frame images A, B, E, and D are synthesized to produce a spatial compound image, thereafter, image synthesis is not performed when reception data corresponding to the sixth frame image E and reception data of the first frame image A in the next data acquisition cycle are acquired, and when reception data of the second frame image is acquired subsequently, five frame images including the frame image B produced based on reception data and the previous four frame images, that is, the fourth frame image D, the fifth frame image C, the sixth frame image E in the previous data acquisition cycle and the first frame image A in the subsequent data acquisition cycle are synthesized to produce a spatial compound image.

In this way, each time reception data of three frame images is acquired, five frame images based on reception data for five frames sequentially acquired hitherto are synthesized to produce a spatial compound image, whereby, among the five frame images for use in producing the spatial compound image, the frame image E is constantly allocated as the frame F3 located at the center in a time-series manner, and the frame images A and C or the frame images D and B are respectively allocated in the first frame F1 and the fifth frame F5 which are most temporally separated.

Figure 7:
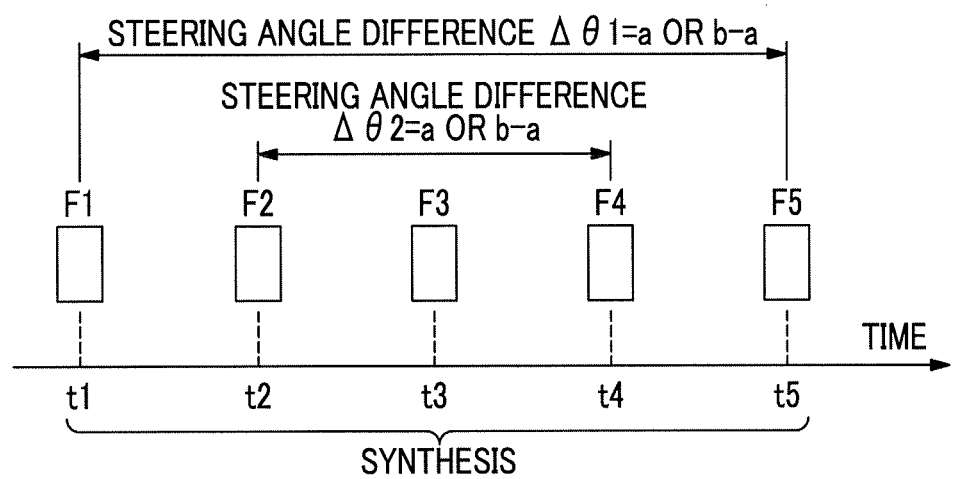
FIG. 7 is a diagram showing the angle difference in steering angle between a first frame and a fifth frame and the angle difference in steering angle between a second frame and a fourth frame among five frame images for use in producing a spatial compound image in Embodiment 2.

That is, as shown in FIG. 7, among the five frame images which are synthesized to produce the spatial compound image, a combination of the first frame F1 for which reception data is acquired at the earliest time t1 and the fifth frame F5 for which reception data is acquired at the latest time t5 becomes the frame image A of the steering angle of 0 degrees and the frame image C of the steering angle +a or the frame image D of the steering angle −b and the frame image B of the steering angle −a, and the angle difference Δθ1 in steering angle between the frame F1 and the frame F5 becomes "a" or "b−a" and is constantly smaller than the maximum angle difference 2·b among the angle difference in steering angle between two frame images among the five kinds of frame images A to E.

Among the five frame images, a combination of the second frame F2 for which reception data is acquired at the second time t2 and the fourth frame F4 for which reception data is acquired at the fourth time t4 becomes the frame image B of the steering angle −a and the frame image D of the steering angle −b or the frame image C of the steering angle +a and the frame image A of the steering angle of 0 degrees, and the angle difference Δθ2 in steering angle between the frame F2 and the frame F4 becomes "b−a" or "a" and is constantly smaller than the maximum angle difference 2·b among the angle differences in steering angle between two frame images among the five kinds of frame images A to E.

For this reason, even if frame images are synthesized five by five to perform spatial compounding while moving the transducer array 1 along the body surface of the subject, a state in which, among the five frame images for use in producing the spatial compound image, the angle difference Δθ1 in steering angle between the first frame F1 and the fifth frame F5, for which the moving distance of the transducer array 1 is largest, and the angle difference Δθ2 in steering angle between the second frame F2 and the fourth frame F4 become the maximum value 2·b is not generated, and it is possible to achieve reduction in artifacts.

The angle difference in steering angle between the first frame F1 and the fourth frame F4 and the angle difference in steering angle between the second frame F2 and the fifth frame F5 are smaller than the maximum angle difference 2·b.

In this way, even if, each time reception data of three frame images is acquired, five frame images based on reception data for five frames sequentially acquired hitherto are synthesized to produce a spatial compound image, among the five frame images for use in producing the spatial compound image, not only the angle difference Δθ1 in steering angle between the first frame F1 and the fifth frame F5 for which the acquisition of reception data is most temporally separated, but also the angle difference Δθ2 in steering angle between the second frame F2 and the fourth frame F4, the angle difference in steering angle between the first frame F1 and the fourth frame F4, and the angle difference in steering angle between the second frame F2 and the fifth frame F5 are smaller than the maximum angle difference 2·b among the angle differences in steering angle between two frame images among the five kinds of frame images A to E. For this reason, even if the frame rate is not increased, it is possible to produce a spatial compound image with reduced artifacts.

The synthesis of frame images is performed each time reception data of three frame images is acquired, and thus, the update rate of the spatial compound image becomes ⅓ compared to a related art example shown in FIG. 12 where frame images are synthesized each time reception data of one frame is acquired. Meanwhile, if frame images are about to be synthesized each time reception data of five frame images for use in producing a spatial compound image is acquired, while the image update rate is lowered to ⅕, it is possible to reduce artifacts while suppressing degradation in operationality.

In Embodiment 2, although reception data corresponding to the frame images A, B, E, D, C, and E are repeatedly acquired in the data acquisition cycle of six frames, and each time reception data of the three frame images E, D, and C or reception data of the three frame images E, A, and B is acquired, five frame images sequentially produced based on reception data for five frames sequentially acquired hitherto are synthesized to produce a spatial compound image, the invention is not limited thereto.

A combination in which, among the five frame images for use in producing the spatial compound image, the frame image D and E are respectively allocated in the first frame F1 and the fifth frame F5, for which the acquisition of reception data is most temporally separated, to form the maximum angle difference 2·b in steering angle should not be used.

For example, reception data of the frame images A, C, D, E, B, and D may be repeatedly acquired in the data acquisition cycle of six frames, and each time reception data of the three frame images D, E, and B or reception data of the three frame images D, A, and C is acquired, five frame images produced based on reception data for five frames sequentially acquired hitherto may be synthesized to produce a spatial compound image. In this case, among the five frame images for use in producing the spatial compound image, a combination of the first frame F1 and the fifth frame F5 for which the acquisition of reception data is most temporally separated becomes the frame image A of the steering angle of 0 degrees and the frame image B of the steering angle −a or the frame image E of the steering angle +b and the frame image C of the steering angle +a, and the angle difference Δθ1 in steering angle between the frame F1 and the frame F5 becomes "a" or "b−a" and is constantly smaller than the maximum angle difference 2·b among the five kinds of steering angles. For this reason, it is possible to reduce artifacts.

A frame image having a maximum steering angle, in this case, either the frame image D of the steering angle −b or the frame image E of the steering angle +b is allocated as a frame image for which reception data is acquired third in the data acquisition cycle of six frames and a frame image for which reception data is acquired sixth. Then, even when five frame images for which reception data is acquired first to fifth in one data acquisition cycle are used to produce a spatial compound image or even when five frame images for which reception data is acquired fourth to sixth in one data acquisition cycle and the first and second frames of the next data acquisition cycle are used to produce a spatial compound image, a frame image having a maximum steering angle for which reception data is acquired third and sixth in the data acquisition cycle is not allocated in the first frame F1 and the fifth frame F5, for which the acquisition of reception data is most temporally separated, among the five frame images for use in producing the spatial compound image, and it is easy to make the angle difference Δθ1 in steering angle between the frames F1 and F5 smaller than the maximum angle difference 2·b among the angle differences in steering angle between two frame images among the five kinds of frame image A to E.

Among the five frame images for use in producing the spatial compound image, the angle difference Δθ1 in steering angle between the first frame F1 and the fifth frame F5 for which the acquisition of reception data is most temporally separated is set to the minimum angle difference among the angle differences in steering angle between two frame images among the five kinds of frame images A to E, whereby it is possible to maximize an artifact reduction effect.

In Embodiment 2, as shown in FIG. 7, among the five frame images which are synthesized to produce the spatial compound image, the angle difference $\Delta\theta 1$ in steering angle between the first frame F1 and the fifth frame F5 for which the acquisition of reception data is most temporally separated becomes the minimum angle difference "b–a" among the angle differences in steering angle between two frame images among the five kinds of frame images A to E or "a" equivalent to the minimum angle difference, and artifacts are effectively reduced.

In Embodiment 2 described above, although, in order to produce a spatial compound image made from five frame images, subsequent to the acquisition of reception data of the first to fifth frame images, reception data having the same steering angle as the third frame image to form a new sixth frame image, and each time reception data of three frame images is acquired, the synthesis of five frame images sequentially produced based on reception data for five frames sequentially acquired hitherto is performed, the invention is not limited thereto.

Figure 8:
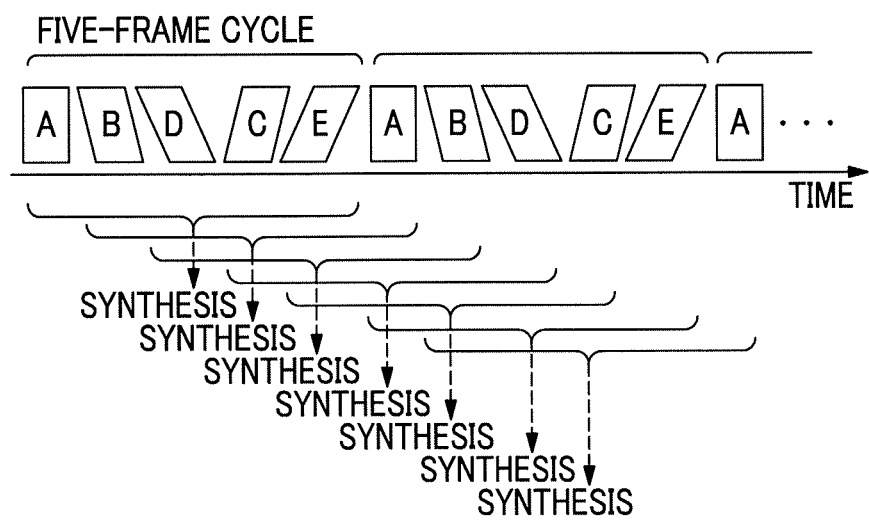
FIG. 8 is a diagram showing the relationship between a data acquisition cycle and frame image synthesis in a modification example of Embodiment 2.

As shown in FIG. 8, reception data corresponding to the frame images A, B, D, C, and E may be repeatedly acquired in a data acquisition cycle of five frames, and each time reception data of one frame image is acquired, five frame images produced based on reception data for five frames sequentially acquired hitherto may be synthesized to produce a spatial compound image.

However, it is necessary to set the order of the frame images of the five kinds of steering angles in each data acquisition cycle such that, among the five frame images for use in producing the spatial compound image, the angle difference $\Delta\theta 1$ in steering angle between the first frame F1 and the fifth frame F5 for which the acquisition of reception data is most temporally separated is constantly smaller than the maximum angle difference 2·b among the angle differences in steering angle between two frame images among the five kinds of frame images A to E.

To this end, the two frame images D and E having the maximum steering angle among the five kinds of frame images A to E should not be respectively allocated as the first and fifth frame images in the data acquisition cycle of five frames or should not be allocated as continuous frame images in the data acquisition cycle. Then, each time reception data of one frame image is acquired, even if five frame images produced hitherto are synthesized, among the five frame images for use in producing the spatial compound image, the frame images D and E having the maximum steering angle are not allocated in both the first frame F1 and the fifth frame F5, and it is possible to achieve reduction in artifacts.

Instead of each time reception data of one frame image is acquired, each time reception data of two or more and four or less frame images is acquired while repeatedly acquiring reception data corresponding to the frame images A, B, D, C, and E in the data acquisition cycle of five frames, five frame images produced based on reception data for five frames sequentially acquired hitherto may be synthesize to produce a spatial compound image. However, as shown in FIG. 8, it is preferable that the synthesis of five frame images is performed each time reception data of one frame image is acquired since the update rate of the spatial compound image is improved and operationality as the ultrasound diagnostic apparatus is increased.

Although the absolute value b of the steering angle of each of the frame images D and E is greater than the absolute value a of the steering angle of each of the frame image B and C, and the angle "b–a" is smaller than the angle a, the invention is not limited thereto. Among the five frame images for use in producing the spatial compound image, the angle difference $\Delta\theta 1$ in steering angle between the first frame F1 and the fifth frame F5 for which the acquisition of reception data is most temporally separated should be smaller than the maximum angle difference among the angle differences in steering angle between two frame images among the five kinds of frame images A to E, and for example, the angle "b–a" may be set to be greater than the angle a.

In Embodiment 2 described above, although the frame images corresponding to the five kinds of steering angles including the frame image A of the steering angle of 0 degrees, the frame image B of the steering angle –a, the frame image C of the steering angle +a, the frame image D of the steering angle –b, and the frame image E of the steering angle +b are produced, the invention is not limited thereto, and five kinds of frame images having different arbitrary steering angles may be produced to produce a spatial compound image.

At this time, among the five kinds of frame images, a frame image having a maximum steering angle is allocated as a frame image for which reception data is acquired third in the data acquisition cycle of six frames and a frame image for which reception data is acquired sixth, whereby, among the five frame images for use in producing the spatial compound image, the angle difference in steering angle between the first frame F1 and the fifth frame F5 for which the acquisition of reception data is most temporally separated can be made smaller than the maximum angle difference among the angle differences in steering angle between two frame images among the five kinds of frame images.

Embodiment 3

In Embodiments 1 and 2 described above, although an odd number of frame images are synthesized to produce a spatial compound image, an ultrasound diagnostic apparatus according to Embodiment 3 synthesizes four frame images to produce a spatial compound image. The configuration of the ultrasound diagnostic apparatus according to Embodiment 3 is the same as the ultrasound diagnostic apparatus of Embodiment 1 shown in FIG. 1.

In Embodiment 3, the frame images B to E corresponding to four kinds of steering angles excluding the frame image A of the steering angle of 0 degrees from the frame images A to E corresponding to the five kinds of steering angles shown in FIG. 5 in connection with the Embodiment 2 are produced.

As will be understood from FIG. 5, the maximum angle difference 2·b among the angle differences in steering angle between two frame images among the four kinds of frame images B to E is formed between the frame image D and the frame image E, and the minimum angle difference "b–a" in steering angle is formed between the frame image B and the frame image D and between the frame image C and the frame image E.

Figure 9:
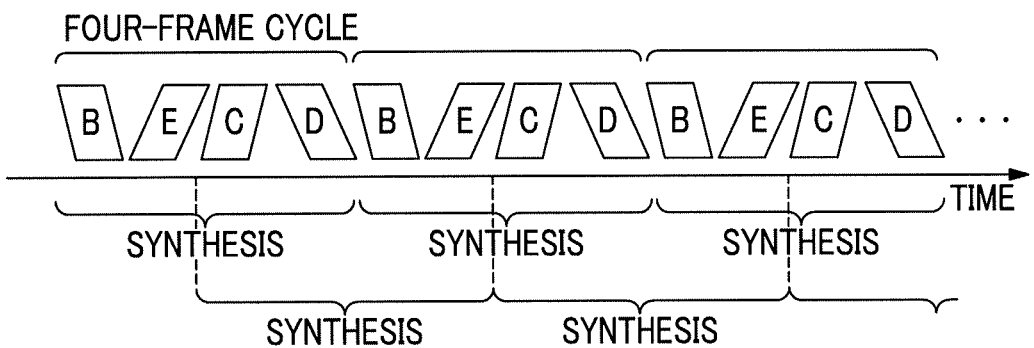
FIG. 9 is a diagram showing the relationship between a data acquisition cycle and frame image synthesis in Embodiment 3.

Then, as shown in FIG. 9, the transmission and reception controller 7 controls the operations of the transmitter 2 and the receiver 3 such that reception data corresponding to the second frame image B of the steering angle –a, reception data corresponding to the third frame image E of the steering angle +b, reception data corresponding to the fifth frame image C of the steering angle +a, and reception data corresponding to the fourth frame image D of the steering angle −b are sequentially repeatedly acquired. That is, reception data corresponding to the frame images B, E, C, and D are repeatedly acquired in the data acquisition cycle of four frames.

The apparatus controller 8 controls the operation of the image synthesizer 22 such that, each time reception data of the two frame images C and D or reception data of the two frame images B and E is acquired, four frame images sequentially produced by the signal processor 21 of the update image producer 4 based on reception data for four frames sequentially acquired hitherto are synthesized to produce a spatial compound image.

For example, if reception data of the fourth frame image is acquired in one data acquisition cycle in which reception data of four frame images is sequentially acquired, four frame images including the frame image D produced based on reception data and the previous three frame images B, E, and C are synthesized to produce a spatial compound image, thereafter, image synthesis is not performed when reception data corresponding to the first frame image is acquired in the next data acquisition cycle, and when reception data of the second frame image is acquired subsequently, four frame images including the frame image E produced based on reception data and the previous three frame images, that is, the third frame image C and the fourth frame image D in the previous data acquisition cycle and the first frame image B in the subsequent data acquisition cycle are synthesized to produce a spatial compound image.

In this way, each time reception data of two frame images is acquired, four frame images based on reception data for four frames sequentially acquired hitherto are synthesized to produce a spatial compound image, whereby, among the four frame images for use in producing the spatial compound image, the frame images B and D or the frame images C and E are respectively allocated in the first frame F1 and the fourth frame F4 for which the acquisition of reception data is most temporally separated.

Figure 10:
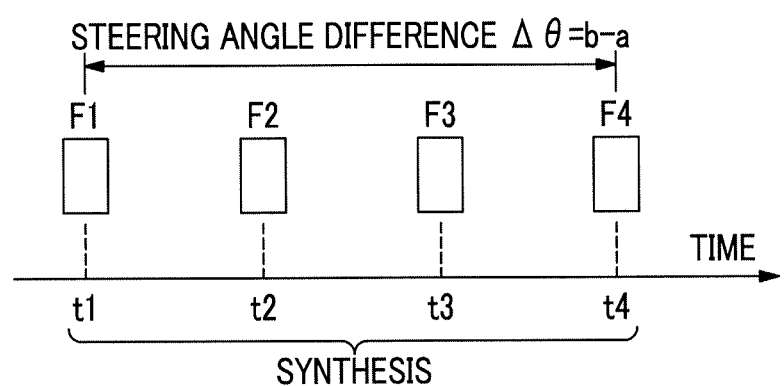
FIG. 10 is a diagram showing the angle difference in steering angle between a first frame and a fourth frame among four frame images for use in producing a spatial compound image in Embodiment 3.

That is, as shown in FIG. 10, among the four frame images which are synthesized to produce the spatial compound image, a combination of the first frame F1 for which reception data is acquired at the earliest time t1 and the fourth frame F4 for which reception data is acquired at the latest time t4 becomes the frame image B of the steering angle −a and the frame image D of the steering angle −b or the frame image C of the steering angle +a and the frame image E of the steering angle +b, and the angle difference Δθ in steering angle between the frame F1 and the frame F4 constantly becomes the minimum angle difference "b−a" among the angle differences in steering angle between two frame images among the four kinds of frame image B to E and is smaller than the maximum angle difference 2·b.

For this reason, even if frame images are synthesized four by four to perform spatial compounding while moving the transducer array 1 along the body surface of the subject, a state in which, among the four frame images for use in producing the spatial compound image, the angle difference Δθ in steering angle between the first frame F1 and the fourth frame F4, for which the moving distance of the transducer array 1 is largest, becomes the maximum value 2·b is not generated, and it is possible to achieve reduction in artifacts.

In this way, each time reception data of two frame images is acquired, even if four frame images based on reception data for four frames sequentially acquired hitherto are synthesized to produce a spatial compound image, among the four frame images for use in producing the spatial compound image, the angle difference Δθ in steering angle between the first frame F1 and the fourth frame F4 for which the acquisition of reception data is most temporally separated is smaller than the maximum angle difference 2·b among the angle differences in steering angle between two frame images among the four kinds of frame images B to E. For this reason, even if the frame rate is not increased, it is possible to produce a spatial compound image with reduced artifacts.

In Embodiment 3, although reception data corresponding to the frame images B, E, C, and D are repeatedly acquired in the data acquisition cycle of four frames, and each time reception data of the two frame images C and D or reception data of the two frame images B and E is acquired, four frame images sequentially produced based on reception data for four frames sequentially acquired hitherto are synthesized to produce a spatial compound image, the invention is not limited thereto.

A combination in which, among the four frame images for use in producing the spatial compound image, the frame images D and E are respectively allocated in the first frame F1 and the fourth frame F4, for which the acquisition of reception data is most temporally separated, to form the maximum angle difference 2·b in steering angle should not be used.

For example, reception data corresponding to the frame images B, D, C, and E may be repeatedly acquired in the data acquisition cycle of four frames, and each time reception data of the two frame images C and E or reception data of the two frame images B and D is acquired, four frame images produced based on reception data for four frames sequentially acquired hitherto may be synthesized to produce a spatial compound image. In this case, among the four frame images for use in producing the spatial compound image, a combination of the first frame F1 and the fourth frame F4 for which the acquisition of reception data is most temporally separated becomes the frame image B of the steering angle −a and the frame image E of the steering angle +b or the frame image C of the steering angle +a and the frame image D of the steering angle −b, and the angle difference Δθ in steering angle between the frame F1 and the frame F4 becomes "a+b" and is constantly smaller than the maximum angle differences 2·b among the four kinds of steering angles. For this reason, it is possible to reduce artifacts.

However, in the data acquisition cycle of the order of the frame images B, E, C, and D shown in FIG. 9, since the angle difference Δθ in steering angle between the frame F1 and the frame F4 becomes the minimum angle difference "b−a" among the angle differences in steering angle between two frame images among the four kinds of frame images B to E, it is possible to more effectively reduce artifacts.

In Embodiment 3 described above, although, in order to produce a spatial compound image made from four frame images, reception data of the four frame images is repeatedly acquired in the data acquisition cycle of four frames, and each time reception data of two frame images is acquired, the synthesis of four frame images sequentially produced based on reception data for four frames sequentially acquired hitherto is performed, the invention is not limited thereto.

Figure 11:
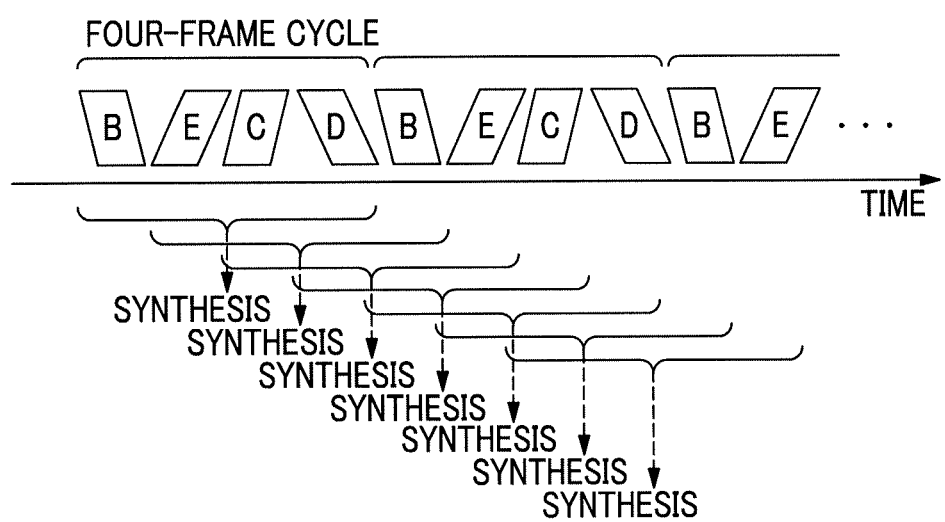
FIG. 11 is a diagram showing the relationship between a data acquisition cycle and frame image synthesis in a modification example of Embodiment 3.

As shown in FIG. 11, reception data corresponding to the frame images B, E, C, and D may be repeatedly acquired in the data acquisition cycle of four frames, and each time reception data of one frame image is acquired, four frame images produced based on reception data for four frames sequentially acquired hitherto may be synthesized to produce a spatial compound image.

However, it is necessary to set the order of frame images of four kinds of steering angles in each data acquisition cycle such that, among the four frame images for use in producing a spatial compound image, the angle difference $\Delta\theta$ in steering angle between the first frame F1 and the fourth frame F4, for which the acquisition of reception data is most temporally separated, is constantly smaller than the maximum angle difference 2·b among the angle differences in steering angle between two frame images among the four kinds of frame images B to E.

To this end, the two frame images D and E having the maximum steering angle among the four kinds of frame images B to E should not be respectively allocated as the first and fourth frame image in the data acquisition cycle of four frames or should not be allocated as continuous frame images in the data acquisition cycle. Then, each time reception data of one frame image is acquired, even if four frame images produced hitherto are synthesized, the frame images D and E having the maximum steering angle among the four frame images for use in producing a spatial compound image are not allocated in both the first frame F1 and the fourth frame F4, and it is possible to achieve reduction in artifacts.

Instead of each time reception data of one frame image is acquired, while reception data corresponding to the frame images B, E, C, and D is repeatedly acquired in the data acquisition cycle of four frames, each time reception data of two or more and three or less frame images is acquired, four frame images produced based on reception data for four frames sequentially acquired hitherto may be synthesized to produce a spatial compound image. However, as shown in FIG. 11, it is preferable that the synthesis of the four frame images is performed each time reception data of one frame image is acquired since the update rate of the spatial compound image is improved and operationality as the ultrasound diagnostic apparatus is increased.

In Embodiment 3, although the frame images corresponding to the four kinds of steering angles including the frame image B of the steering angle −a, the frame image C of the steering angle +a, the frame image D of the steering angle −b, and the frame image E of the steering angle +b are produced, the invention is not limited thereto, and four kinds of frame images having different arbitrary steering angles may be produced to produce a spatial compound image.

Although in Embodiment 1 described above, the three frame images are synthesized to produce a spatial compound image, in Embodiment 2, the five frame images are synthesized to produce a spatial compound image, and in Embodiment 3, the four frame images are synthesized to produce a spatial compound image, the invention can be applied similarly to a case where an odd number of n (seven or more) frame images are synthesized to produce a spatial compound image.

In this case, reception data of n+1 frame images obtained by adding a new frame image having the same steering angle of the ultrasonic beam as a k-th (k=(n+1)/2) specific frame image ordered at the center of n kinds of frame images having different steering angles to n frame images as an (n+1)th frame image can be sequentially repeatedly acquired, and each time reception data of k frame images is acquired, previous n frame images for which reception data is sequentially acquired hitherto can be synthesized to produce a spatial compound image. At this time, a frame image having a maximum steering angle among the n kinds of frame images is used as the k-th specific frame image, among the n frame images for use in producing a spatial compound image, the angle difference in steering angle between two frames for which the acquisition of reception data is most temporally separated can be made smaller than a maximum angle difference among the angle differences in steering angle between two frame images among the n kinds of frame images.

Even when an even number of six or more frame images are synthesized to produce a spatial compound image, similarly, the invention is applied, and among the even number of frame images for use in producing a spatial compound image, the angle difference in steering angle between two frames for which the acquisition of reception data is most temporally separated is smaller than a maximum angle difference among the angle differences in steering angle between two frame images among the even number of frame images, whereby it is possible to reduce artifacts while suppressing degradation in image quality and degradation in image update rate.

In Embodiments 1 to 3 described above, although the image synthesizer 22 of the update image producer 4 synthesizes the B-mode image signal of a plurality of frames produced by the signal processor 21, the invention is not limited thereto, and for example, sound ray signals of a plurality of frames produced through reception focus processing in the signal processor 21 may be synthesized and B-mode image signals may be formed based on the synthesized sound ray signal to produce a spatial compound image.

What is claimed is:

1. An ultrasound diagnostic apparatus comprising:
a transducer array;
a transmitter which supplies an actuation signal to the transducer array to transmit an ultrasonic beam from the transducer array toward a subject;
a receiver which processes a reception signal output from the transducer array having received an ultrasonic echo by the subject to acquire reception data;
a transmission/reception controller which controls the transmitter and the receiver such that, when n is an integer equal to or greater than 3, reception data of n frame images is sequentially repeatedly acquired in order to synthesize the n frame images having different steering angles of the ultrasonic beam to produce an update image, and the angle difference in steering angle between two frame images, for which the acquisition of reception data is most temporally separated, among the n frame images for use in producing the update image is smaller than a maximum angle difference among the angle differences in steering angle between two frame images among the n frame images; and
a processor configured to produce each update image based on reception data acquired by the receiver,
wherein, when m is a constant integer equal to or greater than 1 and less than n, each time reception data of m frame images is acquired by the receiver, the processor synthesizes the previous n frame images, for which reception data is sequentially acquired hitherto, to produce the update image.

2. The ultrasound diagnostic apparatus according to claim 1,
wherein the transmission/reception controller controls the transmitter and the receiver such that the number of the reception data which is repeatedly acquired for producing the update image is larger than the n.

3. The ultrasound diagnostic apparatus according to claim 2, wherein the transmission/reception controller controls the transmitter and the receiver such that the angle difference in steering angle between two frame images, for which the acquisition of reception data is most temporally separated, among the n frame images for use in producing each update image becomes a minimum angle difference among the angle differences in steering angle between two frame images among the n frame images.

4. The ultrasound diagnostic apparatus according to claim 3, wherein when n is an even number, m is n/2.

5. The ultrasound diagnostic apparatus according to claim 2, wherein when n is an even number, m is n/2.

6. The ultrasound diagnostic apparatus according to claim 2, wherein n is 4 and m is 1 or 2, or n is 5 and m is any one of 1 to 3.

7. The ultrasound diagnostic apparatus according to claim 1, wherein the transmission/reception controller controls the transmitter and the receiver such that the angle difference in steering angle between two frame images, for which the acquisition of reception data is most temporally separated, among the n frame images for use in producing each update image becomes a minimum angle difference among the angle differences in steering angle between two frame images among the n frame images.

8. The ultrasound diagnostic apparatus according to claim 1, wherein the transmission/reception controller controls the transmitter and the receiver such that, when n is an odd number, reception data of n+1 frame images obtained by adding a new frame image having the same steering angle of the ultrasonic beam as a k-th (k=(n+1)/2) specific frame image among the n frame images to the n frame images as an (n+1)th frame image is sequentially repeatedly acquired, and each time reception data of k frame images is acquired by the receiver, the processor synthesizes the previous n frame images, for which reception data is sequentially acquired hitherto, to produce the update image.

9. The ultrasound diagnostic apparatus according to claim 1, wherein n is 4 and m is 1 or 2, or n is 5 and m is any one of 1 to 3.

10. An ultrasound image producing method comprising:

performing transmission and reception of an ultrasonic beam by a transducer array such that, when n is an integer equal to or greater than 3, reception data of n frame images is sequentially repeatedly acquired in order to synthesize the n frame images having different steering angles of the ultrasonic beam to produce an update image, and the angle difference in steering angle between two frame images, for which the acquisition of reception data is most temporally separated, among the n frame images for use in producing the update image is smaller than a maximum angle difference among the angle differences in steering angle between two frame images among the n frame images; and producing each update image based on the acquired reception data, wherein, when m is a constant integer equal to or greater than 1 and less than n, each time reception data of m frame images is acquired by a receiver, the previous n frame images, for which reception data is sequentially acquired hitherto, are synthesized to produce the update image.

11. The ultrasound image producing method according to claim 10, wherein the transmission and reception of the ultrasonic beam by the transducer array are performed such that the number of the reception data which is repeatedly acquired for producing the update image is larger than the n.

12. The ultrasound image producing method according to claim 11, wherein the transmission and reception of the ultrasonic beam by the transducer array are performed such that the angle difference in steering angle between two frame images, for which the acquisition of reception data is most temporally separated, among the n frame images for use in producing each update image becomes a minimum angle difference among the angle differences in steering angle between two frame images among the n frame images.

13. The ultrasound image producing method according to claim 12, wherein when n is an even number, m is n/2.

14. The ultrasound image producing method according to claim 11, wherein n is 4 and m is 1 or 2, or n is 5 and m is any one of 1 to 3.

15. The ultrasound image producing method according to claim 10, wherein the transmission and reception of the ultrasonic beam by the transducer array are performed such that the angle difference in steering angle between two frame images, for which the acquisition of reception data is most temporally separated, among the n frame images for use in producing each update image becomes a minimum angle difference among the angle differences in steering angle between two frame images among the n frame images.

16. The ultrasound image producing method according to claim 10, wherein the transmission and reception of the ultrasonic beam by the transducer array are performed such that, when n is an odd number, reception data of n+1 frame images obtained by adding a new frame image having the same steering angle of the ultrasonic beam as a k-th (k=(n+1)/2) specific frame image among the n frame images to the n frame images as an (n+1)th frame image is sequentially repeatedly acquired, and each time reception data of k frame images is acquired by the receiver, the previous n frame images, for which reception data is sequentially acquired hitherto, are synthesized to produce the update image.

17. The ultrasound image producing method according to claim 10, wherein n is 4 and m is 1 or 2, or n is 5 and m is any one of 1 to 3.

* * * * *